United States Patent
Podmore et al.

(10) Patent No.: US 8,573,223 B2
(45) Date of Patent: Nov. 5, 2013

(54) AIRWAY DEVICE WITH TONGUE-ENGAGING MEMBER

(75) Inventors: Jonathan L. Podmore, San Carlos, CA (US); Matthias Vaska, Palo Alto, CA (US); John E. Crowe, Menlo Park, CA (US); Sean Christopher Daniel, Menlo Park, CA (US)

(73) Assignee: Apnicure, Inc., Redwood City, CA (US)

( * ) Notice: Subject to any disclaimer, the term of this patent is extended or adjusted under 35 U.S.C. 154(b) by 224 days.

(21) Appl. No.: 12/840,076

(22) Filed: Jul. 20, 2010

(65) Prior Publication Data

US 2012/0017917 A1    Jan. 26, 2012

(51) Int. Cl.
    *A61F 5/56*         (2006.01)
    *A61C 5/14*         (2006.01)

(52) U.S. Cl.
    USPC .......................................... 128/848; 128/860

(58) Field of Classification Search
    USPC ........................ 128/848, 859–861; 433/6–7
    See application file for complete search history.

(56) References Cited

U.S. PATENT DOCUMENTS

| | | |
|---|---|---|
| 3,132,647 A | 5/1964 | Corniello |
| 4,169,473 A | 10/1979 | Samelson |
| 4,304,227 A | 12/1981 | Samelson |
| 4,676,240 A | 6/1987 | Gardy |
| 5,050,616 A | 9/1991 | Wolff et al. |
| 5,104,315 A | 4/1992 | McKinley |
| 5,465,734 A | 11/1995 | Alvarez et al. |
| 5,915,385 A | 6/1999 | Hakimi |
| 5,957,133 A | 9/1999 | Hart |
| 6,494,209 B2 | 12/2002 | Kulick |
| 6,526,982 B1 | 3/2003 | Strong |
| 6,604,527 B1 | 8/2003 | Palmisano |
| 6,679,257 B1 | 1/2004 | Robertson et al. |
| 6,820,617 B2 | 11/2004 | Robertson et al. |
| 6,877,513 B2 | 4/2005 | Scarberry et al. |
| 6,955,172 B2 | 10/2005 | Nelson et al. |
| 6,976,491 B2 | 12/2005 | D'Agosto |
| 6,997,186 B2 | 2/2006 | Robertson et al. |
| 7,073,505 B2 | 7/2006 | Nelson et al. |
| 7,073,506 B2 | 7/2006 | Robertson et al. |
| 7,182,082 B2 | 2/2007 | Hoffrichter |

(Continued)

FOREIGN PATENT DOCUMENTS

EP        1862152        12/2007

OTHER PUBLICATIONS

Engelke et al., "Preliminary radiographic observations of the tongue-repositioning manoeuvre" Eur. J. of Orthodontics, 2006; 28: 618-623.

(Continued)

*Primary Examiner* — Patricia Bianco
*Assistant Examiner* — Ophelia A Hawthorne
(74) *Attorney, Agent, or Firm* — Wilson, Sonsini, Goodrich & Rosati (57) ABSTRACT

An oral device for improving airway patency having a base adapted to be held between a patient's upper and lower teeth and a tongue-engaging member. The tongue-engaging member engages the tongue and displaces the tongue anteriorly when the base is held between the patient's teeth. A vacuum is applied through the base and the tongue-engaging member in order to draw the soft palate against a posterior region of the tongue in order to stabilize the soft palate and open or clear the patient's airway.

15 Claims, 6 Drawing Sheets

(56) References Cited

U.S. PATENT DOCUMENTS

| | | |
|---|---|---|
| 2001/0047805 A1 | 12/2001 | Scarberry et al. |
| 2005/0166928 A1 | 8/2005 | Jiang |
| 2005/0166929 A1 | 8/2005 | Jiang |
| 2005/0236003 A1 | 10/2005 | Meader |
| 2006/0096600 A1 | 5/2006 | Witt et al. |
| 2006/0282010 A1 | 12/2006 | Martin et al. |
| 2007/0277818 A1 | 12/2007 | Chen |
| 2008/0188947 A1 | 8/2008 | Sanders |
| 2008/0210244 A1 | 9/2008 | Keropian |
| 2008/0216843 A1 | 9/2008 | Jiang |
| 2009/0120446 A1 | 5/2009 | Vaska et al. |
| 2009/0120447 A1 | 5/2009 | Vaska et al. |
| 2009/0123886 A1* | 5/2009 | Vaska .............................. 433/27 |

OTHER PUBLICATIONS

Hoffstein, "Review of oral appliances for treatment of sleep-disordered breathing," Sleep Breath, Mar. 2007;11(1):1-22.

Cartwright et al., "The effects of a non-surgical treatment for obstructive sleep apnea: the tongue retaining device;" JAMA, Aug. 1982; 248(6): 705-709.

International search report and written opinion dated Nov. 16, 2011 for PCT/US2011/043384.

U.S. Appl. No. 13/751,928, filed Jan. 28, 2013, Podmore et al.

* cited by examiner

AIRWAY DEVICE WITH TONGUE-ENGAGING MEMBER

BACKGROUND OF THE INVENTION

1. Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA.

Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the forward end of the patient's mouth, typically at or just behind the lips, to pull the tongue forward in order to lift the rear portion of the tongue away from the back of the airway. See, for example, U.S. Patent Publication Nos. 2007/0277818, 2005/0166928 and 2005/0166929. While promising in theory, in practice it is very difficult to apply a vacuum in the region of the tip of the tongue to raise the base of the tongue and clear the patient's airway, particularly when the patient is lying on his or her back and gravity is pulling the tongue posteriorly. The tongue is a relatively large and compliant organ with significant mass, and applying a vacuum over a relatively small surface area at the tip will often not be effective in raising the back of the tongue against gravity. The moist and compliant tissues in the mouth are somewhat self-sealing, and this effect tends to inhibit the propagation of negative pressure, thereby confining the negative pressures to a relatively small area near the point of application. Thus, simply applying a vacuum at a location near the anterior tip of the tongue tends to draw the tongue up against the hard palate posterior to this location, creating a seal that restricts the propagation of vacuum through this region of contact toward the back of the oral cavity, where direct vacuum is usually required for maximum effectiveness.

As another improvement over CPAP, it has been proposed to place various devices in direct contact with the posterior tissues of the mouth such as the soft palate and posterior portions of the tongue. A major disadvantage of these approaches is that contact with certain tissues near the posterior area of the tongue may elicit the gag reflex and in any case the presence of such devices so far back in the mouth can be uncomfortable.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. Moreover, the methods and devices should avoid contacting the portions of the oral cavity that trigger the gag reflex. The methods and systems should also be simple to implement and be effective to significantly improve patency of a patient's airway during sleep. At least some of these objectives will be met by the inventions described hereinafter.

2. Description of the Background Art

Oral and external devices for treating sleep apnea and snoring are described in U.S. Patent Publication Nos. US2005/166929; US2005/166928; US2008/0188947; US2007/0277818; US2008/0216843; and US2008/0210244; and in U.S. Pat. Nos. 7,182,082; 7,073,506; 7,073,505; 6,955,172; 6,877,513; 6,494,209; 5,957,133; 5,465,734; 4,676,240; 4,304,227; 4,169,473; and 3,132,647; and in Cartwright and Samelson "The effects of a non-surgical treatment for obstructive sleep apnea: the tongue retaining device;" Journal of the American Medical Association 248 (1982). The present invention provides improvements over the devices and methods described in commonly-owned published patent applications 2009/0120446; 2009/0120447; and 2009/123886, the full disclosures of which are incorporated herein by reference.

BRIEF SUMMARY OF THE INVENTION

The present invention provides devices and methods for improving airway patency in patients by engaging a member against the tongue to move the tongue in an anterior direction and allow a vacuum to be drawn between the tongue-engaging member and the soft palate to draw the soft palate away from the pharynx and toward a posterior region of the tongue. By thus drawing the soft palate away from the pharynx, the patient's airway remains clear and the risk of obstructive sleep apnea (OSA) is greatly reduced. The tongue-engaging member is attached to a base and has posterior and anterior surfaces. The anterior surface is inclined forwardly relative to a plane of the base when the base is positioned between the upper and lower teeth and engages a medial region of the tongue to effect anterior tongue displacement. The anterior and posterior surfaces of the tongue-engaging member are usually parallel and inclined at an angle in the range from 45-60° relative to a plane which is defined between the patient's teeth, with the tongue-engaging member extending upwardly from the plane by a distance which is significantly greater than it extends downwardly. This particular geometry, which is described in greater detail hereinbelow, has been found to provide for particularly effective sealing between the soft palate and the posterior region of the tongue with greater patient comfort and reduced risk of inducing the gag reflex.

Oral devices constructed in accordance with the principles of the present invention will include a base, a vacuum conduit, a lip seal, and a tongue-engaging member. The base is adapted to be held between a patient's upper and lower teeth, and the lip seal is coupled to the base and passes the vacuum conduit into the oral cavity. The tongue-engaging member is also coupled with the base and includes an integral plenum which is connected to the vacuum conduit. The tongue-engaging member includes anterior and posterior surfaces, where at the least the anterior surface is inclined forwardly relative to a plane of the base when the base is positioned between the upper and lower teeth and disposed to engage a medial region of the tongue when the base is positioned between the patient's teeth. The tongue-engaging member also includes a plurality of ports distributed over its posterior surface. The ports are open to the plenum and permit a vacuum drawn through the vacuum conduit to be applied to the region between the patient's tongue and the soft palate.

In the exemplary embodiments, the anterior and posterior surfaces of the tongue-engaging member are inclined forwardly (i.e. with the upper end displaced in the anterior direction) at an angle in the range from 45° to 60° relative to a plane of the base when the device is positioned between the upper and lower teeth. Usually, the anterior surface of the member is generally parallel to the posterior surface, and both surfaces will fall within the range of angles set forth above.

The upper edge of the tongue-engaging member will extend at least 5 mm above the plane of the base and from 0 mm to 20 mm in an anterior direction from the patient's molars when the base is positioned between the upper and lower teeth. The tongue-engaging member will have a lower edge which extends up to 8 mm above or below the plane of the base, typically from 0 mm to 5 mm below the plane, and from 0 mm to 5 mm in a posterior direction from the patient's second molars when the base is positioned between the upper and lower teeth. As the tongue-engaging member is typically disk-shaped, more typically having a generally oval periphery, and the body of the base is planar with rounded edges, the member will be able to conform to the patient's natural anatomy by aligning into space between the soft palate and the medial region of the tongue, allowing the area of the member to be maximized while still minimizing the discomfort and risk of gagging.

In the exemplary embodiments, the tongue-engaging member will have an anterior surface which engages the tongue with an area in the range from 300 mm² to 1000 mm², typically from 550 mm² to 750 mm². Usually, although not necessarily, the posterior surface will have an area which is generally in the same range from 450 mm² to 1000 mm², usually from 600 mm² to 850 mm². In certain preferred embodiments, the upper edge of the tongue-engaging member will be curved or otherwise deflected in an anterior direction in order to increase or enhance pushing of the tongue anteriorly when the base is positioned between the upper and lower teeth.

The tongue-engaging member can be positioned at the target region between the medial tongue and the soft palate in a variety of ways. Most commonly, the tongue-engaging member will be supported on a base which comprises a U-shaped bite plate configured to be positioned between the full dentition. The tongue-engaging member can then be positioned between the posterior ends of the legs of the bite plate. Alternatively, the base may comprise left and right molar bite plates which are not joined or held together in other than a U-shaped configuration, where the tongue-engaging member is suspended between the separate bite plates.

In a still further embodiment, the tongue-engaging member may be coupled to and suspended from an axial bridge which joins the tongue-engaging member to a base which is typically held between the patient's front teeth. In still further embodiments, the tongue-engaging member may comprise two or more separate enclosures providing separate plenums, such as a right enclosure and a left enclosure which may be separately joined to left and right portions of the base.

Methods according to the present invention stabilize a soft palate in a patient's oral cavity, typically for the purpose of treating sleep apnea or other breathing disorders. The methods may utilize the apparatus described above or, alternatively, may employ different devices and systems capable of achieving the same soft palate stabilization. An anterior surface of a member is engaged against a medial region of the tongue where the anterior surface is inclined forwardly relative to a plane of the base when the base is positioned between the upper and lower teeth and displaces the medial region in an anterior direction relative to the soft palate to provide a clearance between the soft palate and the tongue, typically the medial region of the tongue. A vacuum is applied within the clearance through a posterior surface of the member, where the vacuum draws together the soft palate in a posterior region of the tongue to move a posterior surface of the soft palate away from the pharynx.

In the specific embodiments, the anterior surface is inclined at an angle in the range from 45° to 60° relative to a bite plane between the patient's upper and lower teeth. The member will have an upper edge and a lower edge, where the lower edge extends up to 8 mm above or below the bite plane and from 0 mm to 5 mm in a posterior direction from the patient's second molars. The upper edge will extend at least 5 mm above the bite plane, and from 0 mm to 20 mm in an anterior direction from the patient's second molars. The anterior surface of the member engages the tongue over an area in the range from 300 mm² to 1000 mm², preferably from 550 mm² to 750 mm², and the vacuum may draw the soft palate against the posterior surface of the member or the soft palate may remain spaced-apart from the posterior surface while the vacuum is being applied. In a particularly preferred configuration, the upper edge of the member is deflected in an anterior direction to increase the anterior displacement of the tongue while the remaining body of the member remains inclined forwardly relative to a plane of the base when the base is positioned between the upper and lower teeth, preferably within the angle of inclination defined above.

The inclination of the cross member as described above allows for the oral device to position the tongue appropriately for vacuum stabilization of the soft palate and tongue, while smoothing the transition of the tongue from a point of initial contact with the roof of the mouth. Such smoothing makes the device more comfortable and positions the tongue more repeatably, improving both patient compliance and device effectiveness.

DETAILED DESCRIPTION OF THE INVENTION

Figure 1:
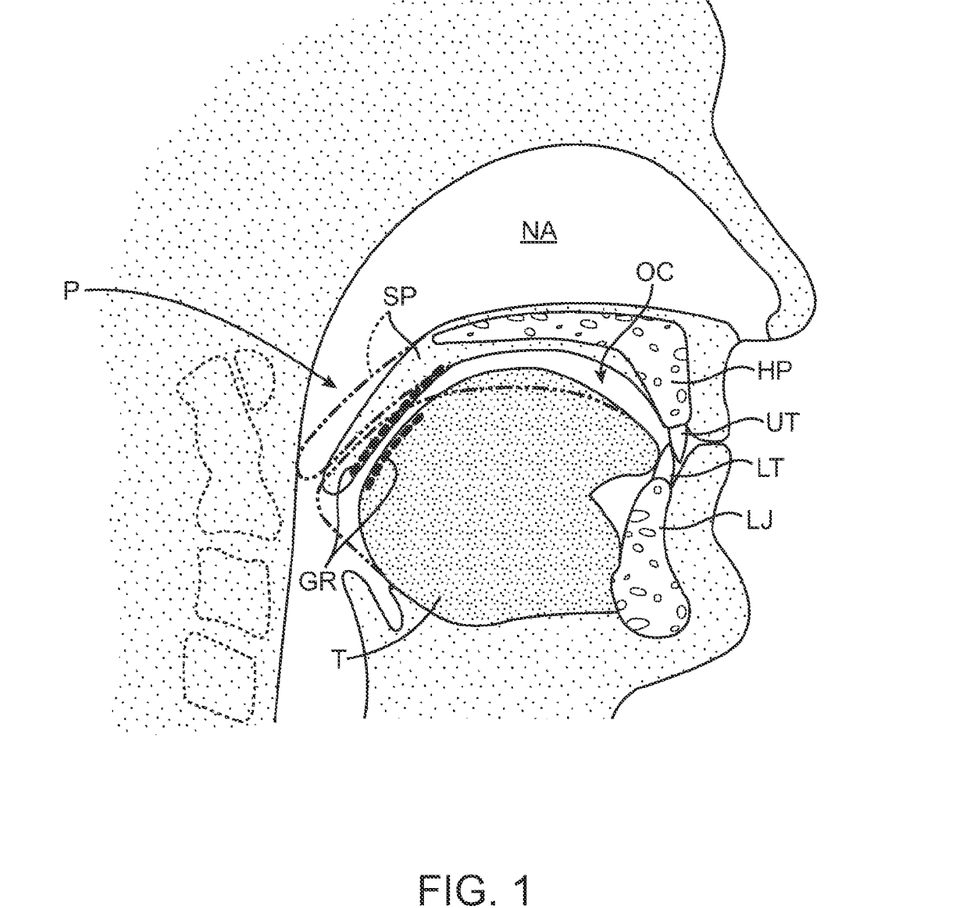
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when either the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

As used herein, "superior" refers to the direction toward the top of the oral cavity (or top of the head), "inferior" refers to the direction opposite the superior direction, "anterior" refers to the direction toward the front of the oral cavity or lips, and "posterior" refers to the direction toward the back of the oral cavity and airway, opposite the anterior direction. The terms "patency" and "airway" refer to the opening or clearing of the airway leading from the nasal cavity into the trachea located generally behind the soft palate and the rear of the tongue. To improve airway patency, the airway may be wholly or partially obstructed intermittently or temporarily for some time period over a normal sleep cycle, however, the airway will be open or partially open more than it would in the patient's untreated condition. The "upper portion of the soft palate" refers to the superior portion of the soft palate extending inferiorly from the end which connects to the hard palate to a point about ⅓-½ way toward the free inferior tip of the soft palate. The phrase "medial region" or "medial surface" of the tongue refers to a superior surface of the tongue which is spaced substantially posteriorly from the anterior tip of the patient's tongue and immediately anterior or forward of the region which initiates the gag reflex. While it may vary from patient to patient, the medial region will generally be the middle one third of the upper surface of the tongue which extends between the anterior tip of the tongue and the posterior end of the tongue (the posterior end being the location on the tongue that is furthest posterior in the oral cavity); i.e., the medial surface will usually include an area of the tongue that is at least about ⅓ of the way, more preferably at least about ½ of the way, from the anterior tip of the tongue to the posterior end of the tongue. Preferably, the medial region will include an area on the tongue posterior to the midpoint between the anterior and posterior ends of the hard palate. The phrase "clear region" refers to the space or volume above and/or posterior of the tongue which will be cleared by the methods and devices of the present invention. The clearing will usually be achieved by engaging a surface which is inclined forwardly relative to a plane of the base when the base is positioned between the upper and lower teeth and against the superior surface of the tongue, typically using a member or element which engages the tongue and which is anchored within the oral cavity so as to simultaneously advance the tongue in an anterior direction and depress the tongue in an inferior direction to open or maintain the clear region and allow the negative pressure to draw the soft palate against the tongue. The term "vacuum" and the phrase "negative pressure" each refers to a total or partial vacuum which is maintained in the clear region, typically by controlled aspiration, where the pressure is maintained primarily in the range from 5 cm $H_2O$ to 150 cm $H_2O$ below the local atmospheric pressure. The "occlusal plane" is the plane in which the upper and lower teeth meet when the patient bites the upper and lower teeth together.

Figure 2A:
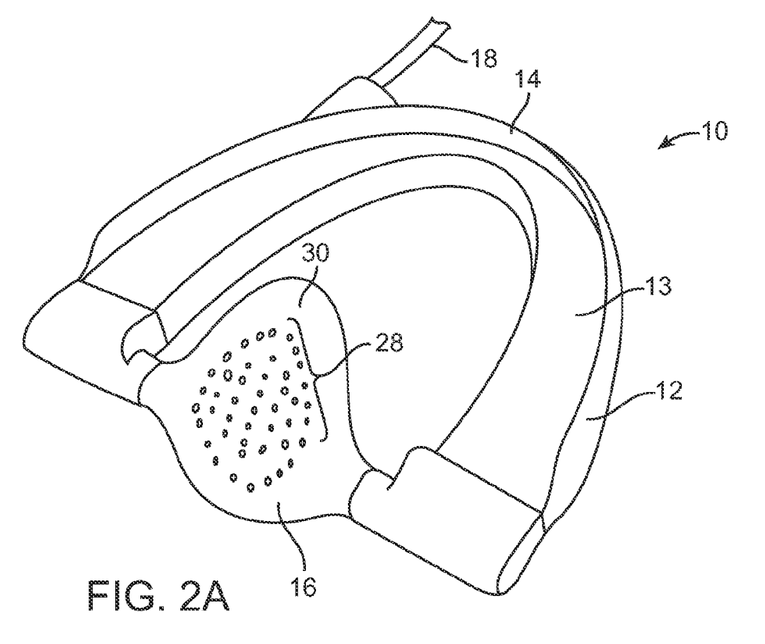
FIGS. 2A and 2B illustrate a first embodiment of an oral device constructed in accordance with the principles of the present invention, with FIG. 2A shown in full line perspective view and FIG. 2B shown with portions broken away.
Figure 2B:
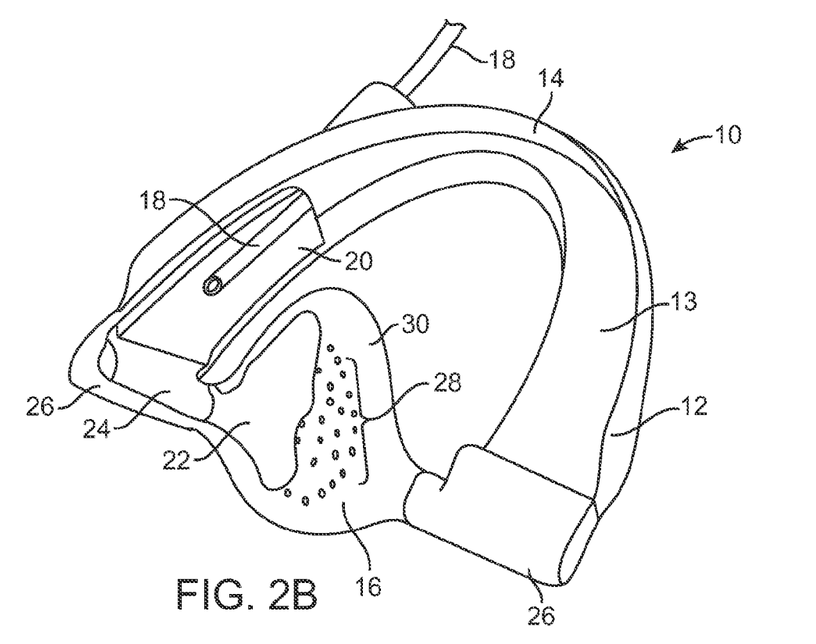

Referring now to FIGS. 2A and 2B, a first exemplary oral device 10 constructed in accordance with the principles of the present invention comprises a U-shaped base or anchor structure 12 having a lip seal 14 at its forward or anterior end. A tongue-engaging member 16 is held between the posterior ends of right and left legs of the U-shaped base 12, and a vacuum tube 18 passes into the device and is open within a plenum 20 in order to draw a vacuum within the device. In particular, the plenum 20 is open to an interior 22 of the tongue-engaging member 16 so that the vacuum may be drawn via a conduit 24 provided through one of the connecting wings 26 which couple the tongue-engaging member 16 to the base 12. A plurality of ports 28 are formed over a posterior surface 30 of the tongue-engaging member 16 so that a vacuum may be applied within the oral cavity when the device 10 is held with the base anchor 12 positioned between the patient's upper and lower teeth. Typically, the patient's teeth will be placed within upper and lower channels 13 (with only the upper channel being shown in FIGS. 2A and 2B) which are formed in the upper or superior and lower or inferior surface of the base 12.

Figure 3:
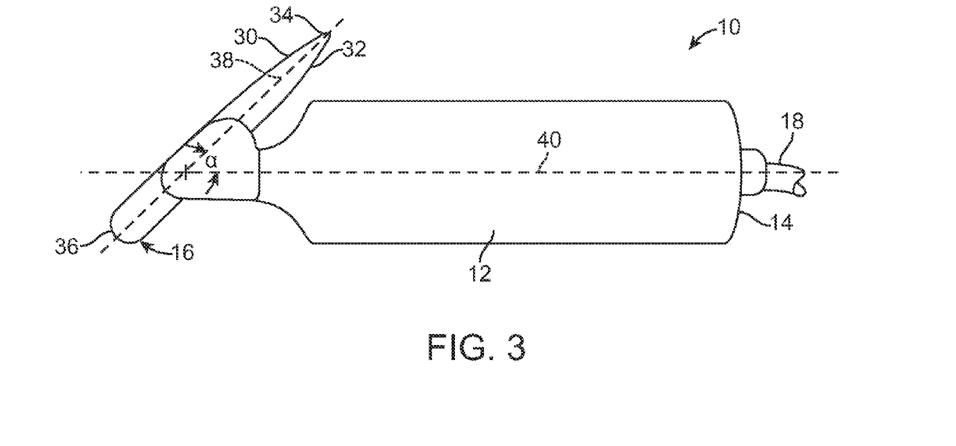
FIG. 3 is a side view of the oral device of FIGS. 2A and 3B.

As best shown in FIG. 3, the tongue-engaging member 16 has both the posterior surface 30 and an anterior surface 32, where the anterior surface will engage the tongue when the base 12 is held between the patient's teeth. The anterior surface of the tongue-engaging member will typically be flat or slightly curved in order to engage a medial region of the tongue over a relatively large surface area, typically in the range from 300 mm² to 1000 mm², usually from 550 mm² to 750 mm². Of particular interest to the present invention, the tongue-engaging member 16 will be inclined with an upper end or lip 34 displaced in an anterior direction (toward the lip seal 14) and a lower or inferior lip or edge 36 being displaced in a posterior direction. The tongue-engaging member 16 will typically have a center line 38 (shown in broken line) which is inclined at an angle α in the range from 30° to 70°, usually from 45° to 60°, relative to a plane 40 (shown in broken line) of the base, which is positioned between the patient's teeth during use of the device. The relatively large area of the anterior surface 32 of the device 10 combined with the angle of inclination, which is generally inclined forwardly relative to a plane of the base when the base is positioned between the upper and lower teeth, combines for particularly effective anterior displacement of the patient's tongue while creating a clear region above the medial region of the tongue in order to apply a vacuum to close the soft palate against the posterior region of the tongue, as described in more detail below.

Figure 4:
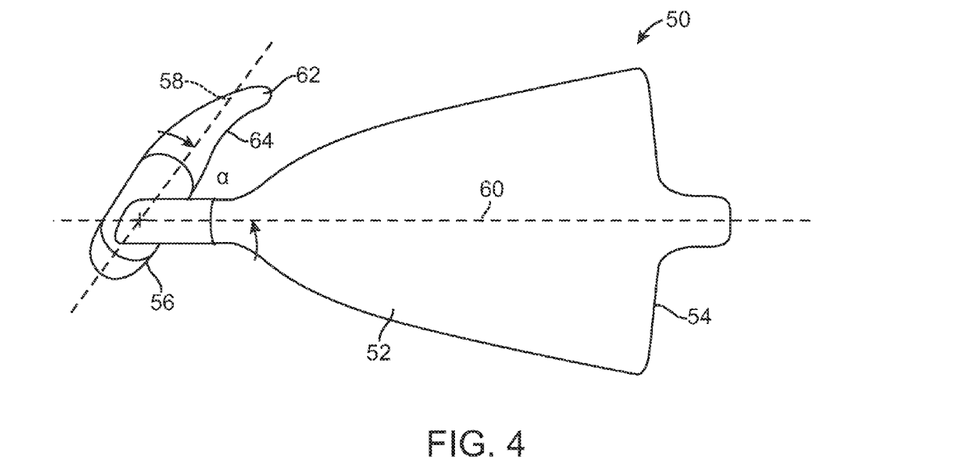
FIG. 4 is a side view of a second embodiment of an oral device constructed in accordance with the principles of the present invention.

Oral device 50 (FIG. 4) represents a second embodiment of the present invention and includes a U-shaped base or anchor 52 having an enlarged lip seal 54 at its anterior end. A tongue-engaging member 56 is carried at the posterior end of the base 52 and has a body which is generally aligned along a plane 58 (shown in broken line) which is disposed at the same angle α relative to the plane of the base 60 (broken line) as with the first device illustrated in FIG. 3. A principal difference of the oral device 50 is that an upper edge 62 of the tongue-engaging member 56 is inclined in a forward or anterior direction, generally with a curved anterior surface 64. The remaining aspects of the oral device 50 are generally the same as described above with respect to the first oral device 10. Use of the oral device 50 is described in more detail in connection with FIGS. 7 and 8.

Figure 5:
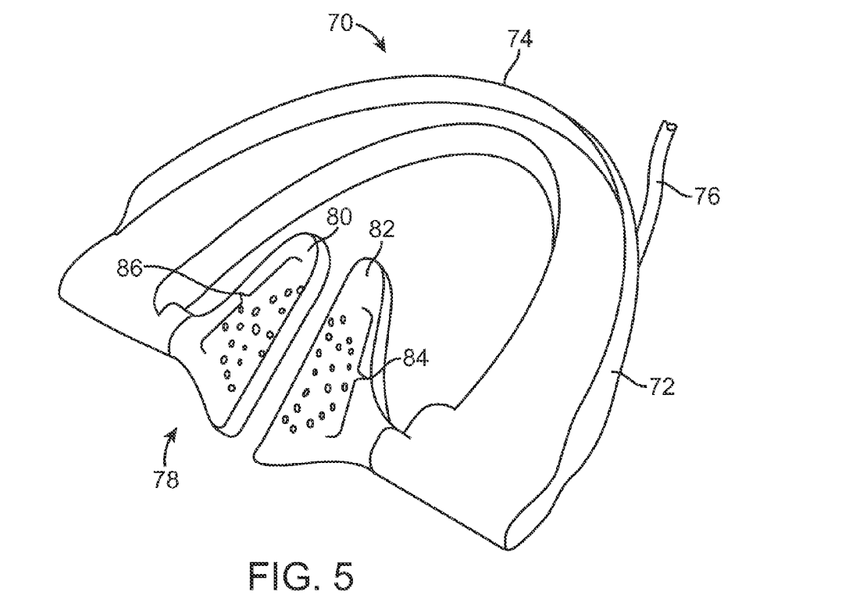
FIG. 5 is a perspective view of a third embodiment of an oral device constructed in accordance with the principles of the present invention.

Referring now to FIG. 5, an oral device 70 comprises a U-shaped base or anchor 72 having a lip seal 74 at its forward or anterior end. A vacuum tube or line 76 is connected to the device in order to apply a vacuum within an interior of the base 72. A tongue-engaging member 78 comprises a right half 80 and a left half 82 (where right and left are viewed from the anterior end of the device which includes the lip seal 74). Each of the right and left halves 80 and 82 are connected to a vacuum plenum (not illustrated) formed through both sides of the interior of base or anchor 72 so that the vacuum applied through vacuum tube 76 is carried through to the ports 84 and 86 formed on the two halves, respectively. The angle of inclination of the two halves will typically be identical, but it could vary by a small amount without departing from the effectiveness of the present invention. The inclination angle(s) and total contact area of the anterior surfaces of the halves 80 and 82 are also within the ranges set forth above, so that the effectiveness of the device is generally the same as described for the previous devices.

Figure 6:
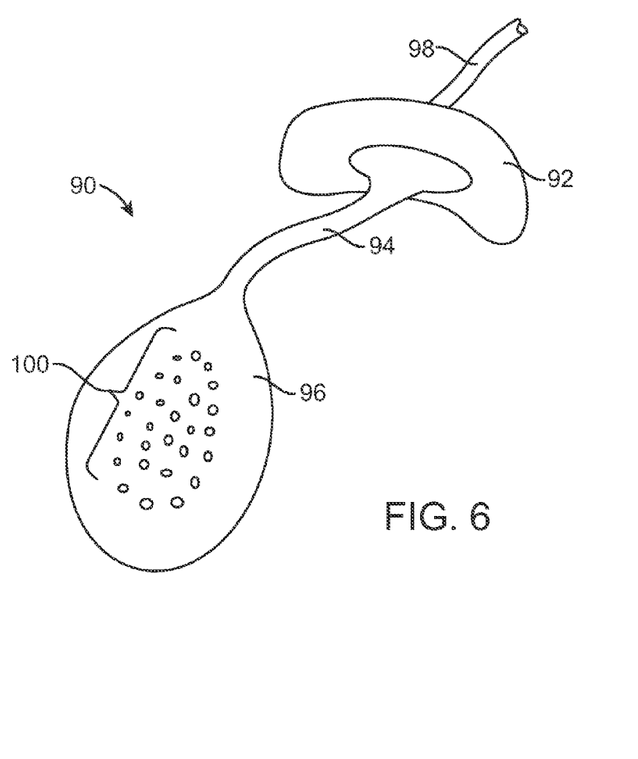
FIG. 6 is a perspective view of a fourth embodiment of an oral device constructed in accordance with the principles of the present invention.

Referring now to FIG. 6, an oral device 90 represents a fourth embodiment of the present invention and comprises an interior bite plate and lip seal 92 connected to a single axial bridge 94 which carries a tongue-engaging member 96 at its posterior end. The tongue-engaging member 96 has generally the same dimensions and is inclined at the same angle relative to a bite plane as described with the prior embodiments. A vacuum is applied through a vacuum tube 98 which is connected via a plenum (not shown) within the single axial member 94 which opens to the interior of the tongue-engaging member 96. The vacuum is applied through a plurality of ports 100. The device 90 is less bulky than the prior embodiments.

Figure 7:
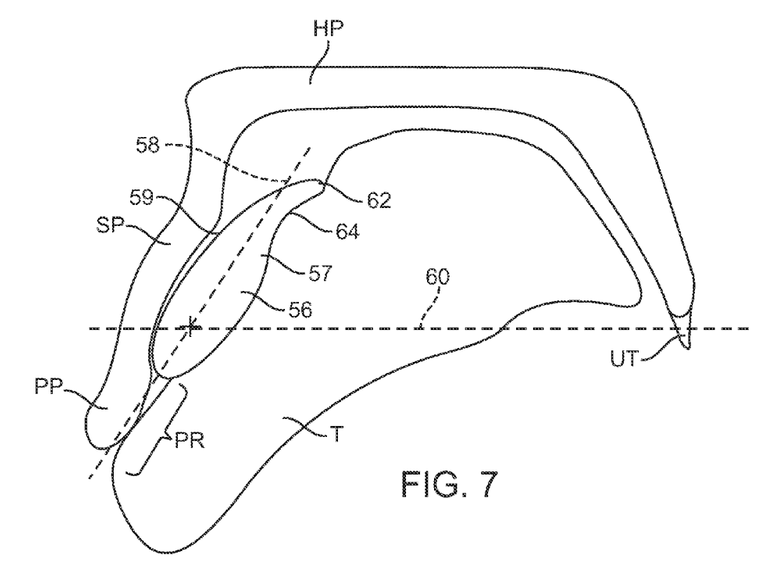
FIGS. 7 and 8 are schematic illustrations of the placement of the oral device of FIG. 4 in an oral cavity with the soft palate engaging a posterior surface of the device in FIG. 7 and the soft palate spaced-apart from the oral device in FIG. 8.
Figure 8:
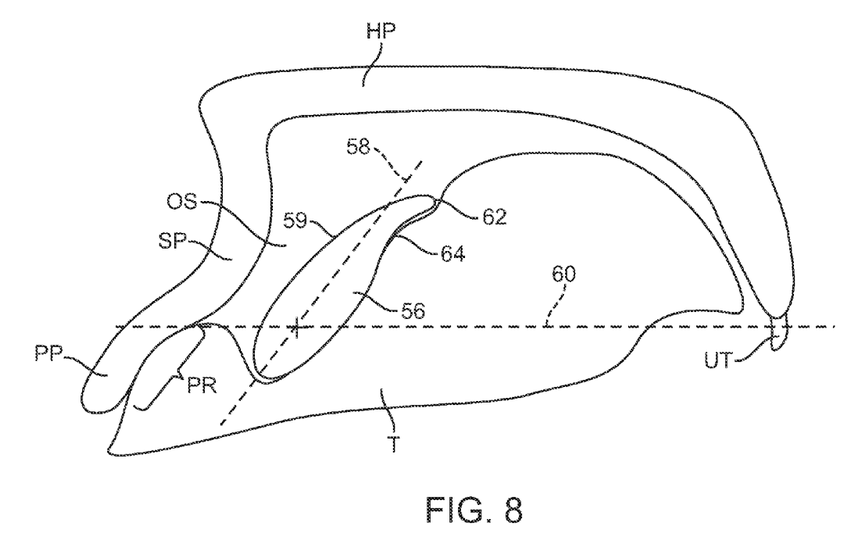

Referring to FIGS. 7 and 8, use of the device 50 for positioning tongue-engaging member 56 against a tongue within an oral cavity will be described. In a first instance, as shown in FIG. 7, anterior surface 57 of the tongue-engaging member 56 engages the medial region of the tongue T to push or displace the tongue in an anterior direction. By applying a vacuum through ports on the posterior surface 59, the soft palate SP is also drawn in an anterior direction so that a posterior portion PP of the palate seals against a posterior region PR of the tongue, as illustrated. The region of the soft palate above the posterior portion is also drawn against the posterior surface 59 of the tongue-engaging member 56, to further stabilize the soft palate to treat the breathing disorder.

The portion of the soft palate SP above the posterior portion PP need not be engaged against the posterior surface 59 of the tongue-engaging member 56. As shown in FIG. 8, an open space OS may remain between the posterior surface 59 and the soft palate SP while the posterior portion PP of the soft palate remains engaged with the posterior region PR of the tongue. The soft palate remains sufficiently stabilized in order to treat the breathing disorders within the methods of the present invention.

Figure 9:
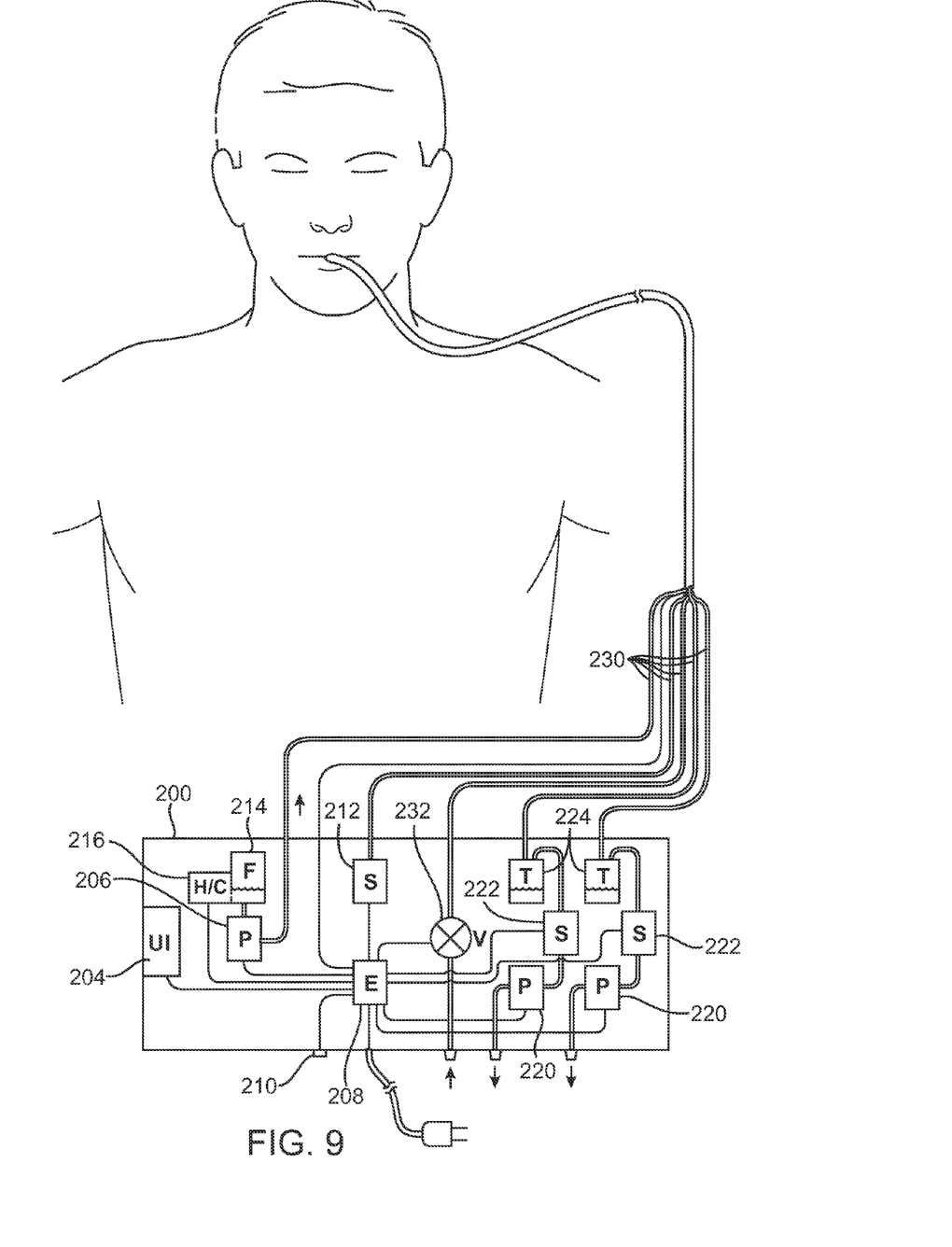
FIG. 9 is a schematic illustration of a control system or console for use in aspirating a negative pressure in the oral devices of the present invention.

A vacuum can be applied to any of these devices via a tabletop control unit 200 having a plurality of tubes 230 connected to the device and which comprises a number of internal components, as best illustrated in FIG. 9. The tabletop control unit will usually include a user interface 204. In order to generate the negative pressure used by the oral devices typically from 25 $cmH_2O$ to 75 $cmH_2O$, described above and to reduce the accumulation of fluid within the mouth, one or more pumps 220, sensors 222 for flow, pressure, or the like and traps 224 will usually be provided. The traps 224 remove saliva and other substances from the tubing to prevent them from entering the pumps 220. The sensors 222 may be used to determine if the device is operating and being applied properly. For example an air leak would generate higher than normal flow and the user could be alerted that there is a problem. Optionally valve 232 may be provided for briefly allowing air to enter the device or oral cavity in order to facilitate aspiration of fluids that have collected in the oral cavity or device. Optionally fluid source 214 and pump 206 for providing moisture and a heater/cooler 216 for heating or cooling the fluid, may be provided. Electronics and power control module 208 will provide for the desired control functions of the unit. Optionally a feedback loop may be configured to monitor the pressure in the oral cavity for example as described above using one of tubes 230 connected to a pressure sensor 212 and to adjust the power of the one or more vacuum pumps 220 in order to maintain the desired level of negative pressure in the oral cavity. Varying distributions of saliva in the tubing that connects the control unit 200 to the oral devices described above will create a pressure differential and such a feedback loop could continually compensate for this varying differential. Optionally, a port 210 may be provided for external connection of the control unit to a computer or data distribution network. Each of these components may be connected to the oral device through appropriate tubes, wires or other connectors 230.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An oral device for temporary placement in a patient's oral cavity, said device comprising;
    a base adapted to be held between a patient's upper and lower teeth;
    a vacuum conduit;
    a lip seal coupled to the base and passing the vacuum conduit into the oral cavity; and
    a tongue-engaging member coupled to the base and having an integral plenum connected to the vacuum conduit, wherein the member has (1) an anterior surface and a posterior surface where the anterior surface is inclined forwardly relative to a plane of the base and is disposed to engage a medial region of the tongue when the base is positioned between the patient's upper and lower teeth, and (2) at least one port on the posterior surface of the tongue-engaging member and open to the plenum;

wherein the tongue-engaging member has an angle of inclination to create a clear region above a medial region of the tongue when the base is positioned between the patient's upper and lower teeth.

2. An oral device as in claim 1, wherein the anterior surface of the tongue-engaging member is generally parallel to the posterior surface of the member.

3. An oral appliance as in claim 2, wherein the tongue-engaging member has a lower edge which extends up to at least 8 mm above or below the plane of the base and from 0 mm to 5 mm in a posterior direction a location on the base intended to be positioned between the patient's second molars when the base is positioned between the upper and lower teeth.

4. An oral appliance as in claim 3, wherein the tongue-engaging member has an upper edge which extends at least 5 mm above the plane of the base and from 0 mm to 20 mm in an anterior direction from the location on the base intended to be positioned between the patient's second molars when the base is positioned between the upper and lower teeth.

5. An oral appliance as in claim 3, wherein the posterior surface includes a cross member having an area in a range from 600 mm$^2$ to 850 mm$^2$.

6. An oral device as in claim 1, wherein the tongue-engaging member has a plurality of ports distributed over the posterior surface thereof.

7. An oral device as in claim 1, wherein the surfaces of the member are inclined forwardly at an angle in a range from 45° to 60° relative to a plane of the base when positioned between the upper and lower teeth.

8. An oral appliance as in claim 1, wherein the base comprises a U-shaped bite plate configured to be positioned between the full dentition.

9. A method for stabilizing a soft palate in a patient's oral cavity, said method comprising:

engaging an anterior surface of a member against a medial region of a tongue, wherein the anterior surface is inclined forwardly relative to a plane of a base when the base is held between a upper and lower teeth to displace the medial region of the tongue in an anterior direction relative to the soft palate to provide a clearance therebetween, wherein a region above a medial region of the tongue remains clear; and applying a vacuum within the clearance through a posterior surface of the member to draw together the soft palate and a posterior region of the tongue.

10. A method as in claim 9, wherein the anterior surface is inclined at an angle in a range from 45° to 60° relative to a bite plane between the patient's upper and lower teeth.

11. A method as in claim 10, wherein the member has a lower edge which extends up to 8 mm above or below the bite plane and from 3 mm to 5 mm in a posterior direction from a location on the base intended to be positioned between the patient's second molars.

12. A method as in claim 11, wherein the member has an upper edge which extends at least 5 mm above the bite plane and from 0 mm to 20 mm in an anterior direction from a location on the base intended to be positioned between the patient's second molars.

13. A method as in claim 11, wherein the anterior surface engages the tongue over an area in a range from 550 mm2 to 750 mm2.

14. A method as in claim 9, wherein the vacuum draws the soft palate against the posterior surface of the member.

15. A method as in claim 9, wherein the soft palate remains spaced-apart from the posterior surface of the member while the vacuum is being applied.

* * * * *